(12) United States Patent
Trachsler et al.

(10) Patent No.: US 9,517,079 B2
(45) Date of Patent: Dec. 13, 2016

(54) TIBIAL RESECTION SYSTEMS AND METHODS FOR CRUCIATE LIGAMENT RETAINMENT

(71) Applicant: Zimmer, Inc., Warsaw, IN (US)

(72) Inventors: Thomas Trachsler, Kefikon (CH);
Michael Hörth, Winterthur (CH);
Herve Houdemer, Zurich (CH)

(73) Assignee: Zimmer, Inc., Warsaw, IN (US)

( * ) Notice: Subject to any disclaimer, the term of this patent is extended or adjusted under 35 U.S.C. 154(b) by 394 days.

(21) Appl. No.: 14/195,323

(22) Filed: Mar. 3, 2014

(65) Prior Publication Data

US 2014/0257310 A1    Sep. 11, 2014

Related U.S. Application Data

(60) Provisional application No. 61/774,296, filed on Mar. 7, 2013.

(51) Int. Cl.

| | | |
|---|---|---|
| *A61B 17/58* | (2006.01) | |
| *A61B 17/60* | (2006.01) | |
| *A61F 2/00* | (2006.01) | |
| *A61B 17/17* | (2006.01) | |
| *A61B 17/15* | (2006.01) | |
| *A61B 17/16* | (2006.01) | |

(52) U.S. Cl.
CPC ......... *A61B 17/1764* (2013.01); *A61B 17/157* (2013.01); *A61B 17/1604* (2013.01); *A61B 17/1675* (2013.01); *A61B 17/1735* (2013.01)

(58) Field of Classification Search
None
See application file for complete search history.

(56) References Cited

U.S. PATENT DOCUMENTS

| | | | |
|---|---|---|---|
| 8,728,086 B2 | 5/2014 | Smith et al. | |
| 8,728,167 B2 | 5/2014 | Collazo | |
| 2010/0331848 A1* | 12/2010 | Smith .................. | A61B 17/155 606/88 |
| 2012/0316563 A1 | 12/2012 | Metzger et al. | |

FOREIGN PATENT DOCUMENTS

| | | |
|---|---|---|
| WO | WO-2010138854 A2 | 12/2010 |
| WO | WO-2010147797 A2 | 12/2010 |
| WO | WO-2012158604 A1 | 11/2012 |

* cited by examiner

*Primary Examiner* — Sameh Boles
(74) *Attorney, Agent, or Firm* — Schwegman Lundberg & Woessner, P.A.

(57) ABSTRACT

Tibial resection systems and methods for use in a uni- or bi-cruciate retaining knee replacement procedure are disclosed. A tibial resection system can include a tibial block, an alignment guide, and a tibial implant template. The tibial block can be coupled to an anterior side of a tibia and longitudinally extend from a proximal end portion to a distal end portion. The alignment guide can be coupled to the proximal end portion of the tibial block and can include one or more drill guides and a drill guide adjustment mechanism. The tibial implant template can be engaged with the drill guide adjustment mechanism, such that rotational movement of the tibial implant template can adjust an axial direction of the one or more drill guides. An outer profile of the tibial implant template can be selected to substantially match an outer profile of a tibial prosthesis to be implanted.

11 Claims, 18 Drawing Sheets

TIBIAL RESECTION SYSTEMS AND METHODS FOR CRUCIATE LIGAMENT RETAINMENT

CLAIM OF PRIORITY

This application claims the benefit of U.S. Provisional Patent Application Ser. No. 61/774,296, filed on Mar. 7, 2013, the benefit of priority of which is claimed hereby, and of which is incorporated by reference herein in its entirety.

TECHNICAL FIELD

This document pertains generally, but not by way of limitation, to tibial resection systems and methods.

BACKGROUND

Retaining one or both of an Anterior Cruciate Ligament (ACL) and a Posterior Cruciate Ligament (PCL) in a knee replacement procedure can lead to shorter recovery times and a less invasive surgical procedure.

Existing systems and methods used to preserve an ACL or PCL during a surgical procedure, such as those disclosed in WO 2010/138854, WO 2010/147797, and US 2010/0331848, are complex, can be difficult for a surgeon to use, and may not provide for stable or accurate bone cuts.

OVERVIEW

This patent document pertains generally to systems and methods that can be used in a uni- or bi-cruciate retaining tibial resection procedure, such as during a total knee replacement surgery, in a more simplistic, stable, and accurate way than is currently available. The present inventors recognize that existing cruciate retaining tibial resection systems and methods fail to provide a surgeon with the ability to accurately produce a proximal tibial resection using a template, relating to a size or shape of a tibial prosthesis to be implanted, to orient one or more drill guides. The present inventors also recognize that existing cruciate retaining tibial resection systems and methods fail to provide a surgeon with the ability to produce a resected bone block with a radiused corner on lateral, medial, and/or anterior sides of the tibia. It is believed that radiused corners of the tibial bone block can provide greater bone stability than stress-focusing sharp-edged corners.

Through the use of the present systems and methods, a surgeon can accurately envision the proper size, shape, and/or placement of a tibial prosthesis that allows for retaining one or both the ACL and PCL. Because a tibial implant template can be engaged with a drill guide adjustment mechanism, which can form the basis of resection saw blade cuts, the correct placement of the saw blade cuts can be provided.

The present patent document also discloses systems and methods for ensuring that edges and inside corners of a resected tibial bone block are rounded or radiused, thereby providing greater bone stability. A chisel and mill guide and a chisel can be used to produce an anterior cut in a tibial bone block. The chisel and mill guide used in conjunction with the chisel can ensure that an anterior inside corner can be milled in a rounded manner. Use of the chisel as a forward stop can prevent a mill from over cutting the tibial bone block.

To better illustrate the tibial resection systems and methods disclosed herein, a non-limiting list of examples is provided here:

In Example 1, a tibial resection system can comprise a tibial block, an alignment guide, and a tibial implant template. The tibial block can be coupled to an anterior side of a tibia and longitudinally extend from a proximal end portion to a distal end portion. The alignment guide can be coupled to the proximal end portion of the tibial block and can include one or more drill guides and a drill guide adjustment mechanism. The tibial implant template can be engaged with the drill guide adjustment mechanism, such that rotational movement of the tibial implant template adjusts an axial direction of the one or more drill guides.

In Example 2, the tibial resection system of Example 1 can optionally be configured such that the proximal end portion of the tibial block includes a guide surface having a slot. The slot can extend in a direction perpendicular to the longitudinal extension of the tibial block and can be configured to receive a coupling projection of the alignment guide.

In Example 3, the tibial resection system of Example 2 can optionally be configured such that the slot includes a T-shaped cross-section. The coupling projection can include a size and a shape engageable with the T-shaped cross-section.

In Example 4, the tibial resection system of any one or any combination of Examples 1-3 can optionally be configured such that an outer profile of the tibial implant template substantially matches an outer profile of a tibial prosthesis to be implanted.

In Example 5, the tibial resection system of any one or any combination of Examples 1-4 can optionally be configured such that the tibial implant template includes a plurality of tibial implant templates having differing outer profile shapes or sizes.

In Example 6, the tibial resection system of any one or any combination of Examples 1-5 can optionally be configured such that the tibial implant template is sized and shaped to fit in situ between a proximal end of the tibia and a distal end of a femur, between medial and lateral collateral ligaments, and partially around one or more cruciate ligaments.

In Example 7, the tibial resection system of any one or any combination of Examples 1-6 can optionally be configured such that the tibial implant template includes one or more holes positioned to match a location of one or more holes of a tibial prosthesis to be implanted.

In Example 8, the tibial resection system of any one or any combination of Examples 1-7 can optionally be configured such that the alignment guide comprises a first member, including the one or more drill guides, and a second member positioned proximally of the first member. The first and second members can be pivotably connected and moveable, relative to one another, using the drill guide adjustment mechanism.

In Example 9, the tibial resection system of any one or any combination of Examples 1-8 can optionally further comprise one or more guide pins insertable into one or more drill holes formed using the one or more drill guides.

In Example 10, the tibial resection system of Example 9 optionally further comprise a cutting guide, positionable on the one or more guide pins, including one or more vertical cut slots and one or more horizontal cut slots.

In Example 11, the tibial resection system of Example 10 can optionally be configured such that the one or more horizontal cut slots and the one or more vertical cut slots are positioned to align with an outer surface of the one or more guide pins, when the cutting guide is positioned thereon.

In Example 12, the tibial resection system of any one or any combination of Examples 1-11 can optionally further comprise a chisel and mill guide having a proximal end portion, including a pin projection and a curved recess wall; a distal end portion, positionable on a resected tibial surface; and an anterior portion, including a mill recess.

In Example 13, the tibial resection system of Example 12 can optionally be configured such that the pin projection is configured to receive a mating void of a chisel handle and the curved recess wall is configured to receive and guide a chisel blade.

In Example 14, the tibial resection system of any one or any combination of Examples 12 or 13 can optionally be configured such that an extension of the curved recess wall intersects with a depth of the mill recess.

In Example 15, a tibial resection method comprises attaching a tibial block to a tibia; securing an alignment guide, including one or more drill guides and a drill guide adjustment mechanism, to the tibial block; selecting a tibial implant template to match a size or shape of a proximal end of the tibia; and engaging the selected tibial implant template with the drill guide adjustment mechanism. The tibial resection method can further comprise moving the selected tibial implant template to a desired position on the proximal end of the tibia, including adjusting an axial direction of the one or more drill guides; and drilling one or more guide pin holes in the tibia using the one or more drill guides.

In Example 16, the tibial resection method of Example 15 can optionally be configured such that drilling the one or more guide pin holes includes forming a radius corner of a resection cut.

In Example 17, the tibial resection method of any one or any combination of Examples 15 or 16 can optionally further comprise removing the alignment guide; inserting a guide pin in each of the one or more guide pin holes; positioning a cutting guide on the one or more guide pins, including aligning one or more vertical cut slots and one or more horizontal cut slots with an outer surface of the one or more guide pins; resecting tibial bone along the one or more vertical cut slots and the one or more horizontal cut slots, including preserving an anterior cruciate ligament and a posterior cruciate ligament; and removing the cutting guide.

In Example 18, the tibial resection method of Example 17 can optionally be configured such that attaching the tibial block to the tibia includes establishing a height of the one or more horizontal cut slots.

In Example 19, the tibial resection method of any one or any combination of Examples 17 or 18 can optionally further comprise attaching a chisel and mill guide to the tibia, including positioning a first portion of the chisel and mill guide on a medial side of the anterior and posterior cruciate ligaments and positioning a second portion of the chisel and mill guide on a lateral side of the anterior and posterior cruciate ligaments.

In Example 20, the tibial resection method of Example 19 can optionally further comprise chiseling an anterior portion of the proximal end of the tibia, including guiding a chisel distally along a pin projection extending from a proximal end portion of the chisel and mill guide; and, after chiseling, milling a base of the anterior portion of the proximal end of the tibia, including guiding a milling tool along a mill recess on an anterior portion of the chisel and mill guide.

In Example 21, the tibial resection method of Example 20 can optionally be configured such that guiding the milling tool along the mill recess includes protecting a portion of the proximal end of the tibia using a portion of the chisel.

In Example 22, the tibial resection method of any one or any combination of Examples 15-21 can optionally be configured such that selecting the tibial implant template includes sliding a tibial implant template between the proximal end of the tibia and a distal end of a femur, between medial and lateral collateral ligaments, and partially around one or more cruciate ligaments.

These and other examples and features of the present tibial resection systems and methods will be set forth, in part, in the following Detailed Description. This Overview is intended to provide non-limiting examples of the present subject matter—it is not intended to provide an exclusive or exhaustive explanation. The Detailed Description below is included to provide further information about the present tibial resection systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present patent document.

DETAILED DESCRIPTION

Figure 1:
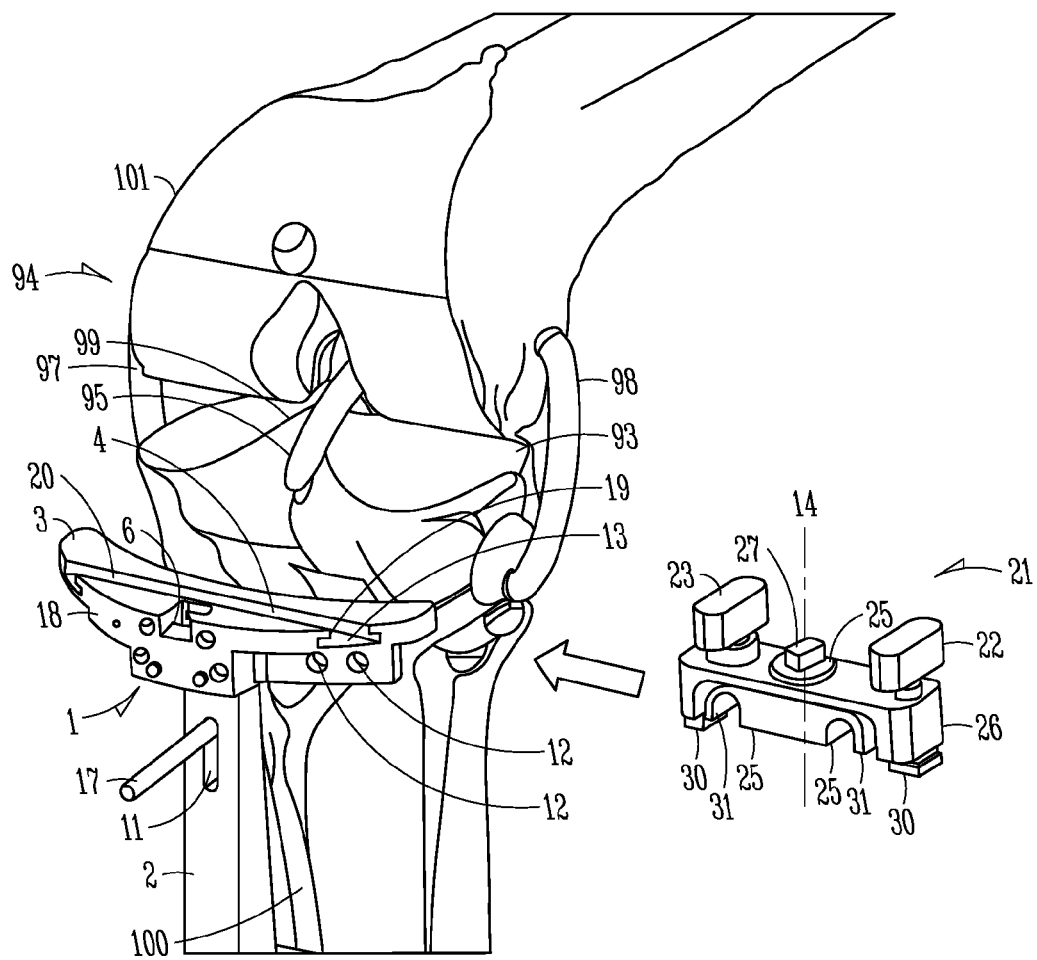
FIG. 1 illustrates a schematic view of a tibial block, in position for a tibial resection procedure, and the advancement of an alignment guide onto a proximal end portion of the tibial block.

FIG. 1 illustrates a knee joint 94 including a distal end of a femur 101, a proximal end of a tibia 93, and several ligaments, including an anterior cruciate ligament (ACL) 95 on a front side of the tibia 93. A posterior cruciate ligament (PCL) is hidden, but is in an analogous position to the ACL 95, on a back side of the tibia 93. A medial collateral ligament (MCL) 97 is located on an inner side of the knee joint 94 and a lateral collateral ligament (LCL) 98 is located on an outer side of the knee joint 94. The proximal end of the tibia 93 can include an uneven top surface and can have one or more protrusions in the area of an intercondylar eminence 99.

Figure 3:
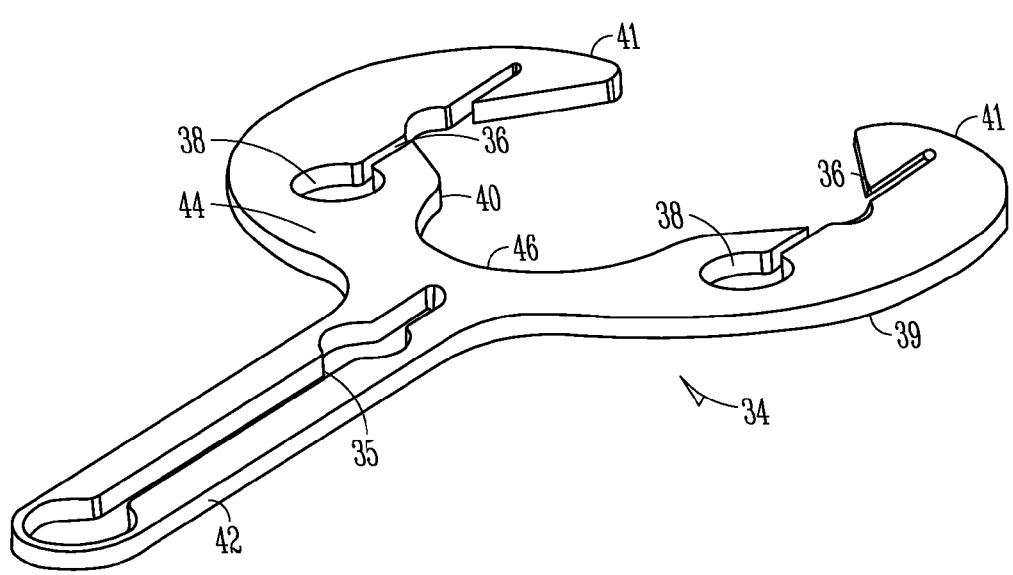
FIG. 3 illustrates an isometric view of a tibial implant template.

A tibial resection system can include, among other things, a tibial block 1, an alignment guide 21, and a tibial implant template 34 (FIG. 3).

The tibial block 1 can be secured to an anterior side 100 of the tibia 93. The connection can be accomplished by one or more tibial block pins 17, for example. Alternatively, the tibial block 1 can be secured to the tibia 93 by screws, bolts, nails, or straps. The tibial block 1 can include a longitudinal extension 2 configured to provide vertical support to a horizontal member 18, located at a proximal end portion of the tibial block 1. The longitudinal extension 2 can include an adjustment slot 11 that can be used to adjust the position of the tibial block 1 after a tibial block pin 17, or other securing means, has been installed. The longitudinal extension 2 and the horizontal member 18 can include a plurality of attachment holes 12, which can be used to further secure the tibial block 1 to the tibia 93.

The horizontal member 18 of the tibial block 1 can include an alignment guide retaining structure 20, which can be configured as a slot 4. The slot 4 can take the form of an inverted "T" in cross-section, with a base 13 having a greater width than a neck region 19 and configured to receive one or more coupling projections 30 on the alignment guide 21. In an alternative example, the mating structures can be reversed with a "T"-shaped rail disposed on the horizontal member 18 and a coupling projection, such as a slot, in the alignment guide 21. The horizontal member 18 can include a horizontal, planar guide surface 3. A tibial block alignment structure 6 can be located on the horizontal member 18. The tibial block alignment structure 6 can engage a handle (not shown) to align the tibial block 1 with the tibia 93.

Once the tibial block 1 has been secured in a desired position, the alignment guide 21 can be positioned on the horizontal, planar guide surface 3. A surgeon can position the alignment guide 21 at any position along the slot 4 and can use a relative position of the ACL 95 as a guide.

Figure 2:
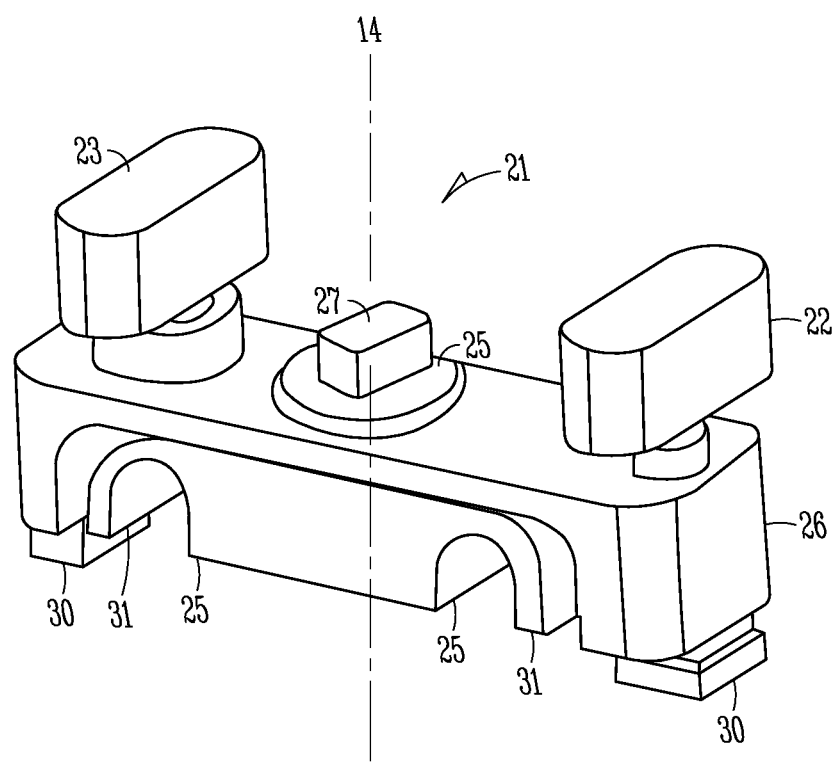
FIG. 2 illustrates an isometric view of an alignment guide.

FIG. 2 illustrates an enlarged view of an alignment guide 21, relative to the illustration of FIG. 1. The alignment guide 21 can include one or more drill guides 31, which allow accurate placement of one or more drill holes in the tibia 93. The one or more drill guides 31 can be coupled with a drill guide adjustment mechanism 27.

The drill guides 31 and the drill guide adjustment mechanism 27 together form a first member 25 of the alignment guide 21, which is disposed distally of a second member 26 of the alignment guide 21. The second member 26 can provide a structural framework for the moving portions of the alignment guide 21, including the first member 25. In operation, the second member 26 can be secured to the tibial block 1 in a manner that allows the first member 25 to move while the second member 26 remains stationary. The alignment guide 21 can include a first tightening screw 22 with a coupling projection 30 on its distal end. When the alignment guide 21 has been disposed on the tibial block 1 and positioned as desired, the first tightening screw 22 can be tightened and the second member 26 and the alignment guide 21 can no longer move relative to the tibial block 1. However, the first member 25 is still free to rotate about an axis 14 and the drill guides 31 can be adjusted to a correct angular direction by movement of the drill guide adjustment mechanism 27. When the proper angular position of the drill guides has been achieved, a second tightening screw 23 of the alignment guide 21 can be tightened and the drill guides 31 can be secured for a drill guiding operation.

By way of example, the first tightening screw 22 can be a T-slot bolt which, when tightened, secures the second member 26 to the tibial block 1, but does not affect movement of the drill guides 31. The second tightening screw 23, when tightened, can bear down upon a surface of the drill guides 31 while causing a coupling projection 30 connected to the second member 26 to be lifted against a surface of the alignment guide retaining structure 20 (see FIG. 1). The drill guides 31 can then be immovable between the second tightening screw 23 and the planar guide surface 3 (see FIG. 1).

FIG. 3 illustrates a tibial implant template 34. The tibial implant template 34 can be generally flat and planar and can be sized and shaped to fit between the proximal end of the tibia 93 and the distal end of the femur 101 (see FIG. 1). The tibial implant template 34 can include two regions, a body 44 and a long axis member 42.

The body 44 can be generally shaped to match the proximal end of the tibia 93. The outer profile 39 of the body 44, for example, can be shaped to match the shape of a tibial prosthesis (not shown) that a surgeon intends to implant during a knee surgical procedure. An inner profile 40 of the body 44 can be shaped to accommodate the proximal end of the tibia 93, which can include an uneven surface and can have one or more protrusions in the area of an intercondylar eminence 99 (see FIG. 1). The inner profile 40 can also be shaped to allow placement of the tibial implant template 34 without disturbance to the ACL 95 (see FIG. 1), such as by way of an ACL recess 46. Because the tibial implant template 34 can be moved in a posterior direction until it approximates the placement of the tibial prosthesis, an opening between two arms 41 allows for movement without disturbance to the ACL 95 (see FIG. 1). The arms 41 can be configured in a pincer-like or forked formation and not only allow a surgeon to envision the placement of a tibial prosthesis, but can also provide the surgeon with a method to visualize the distance of a tibial prosthesis from a PCL.

The long axis member 42 can include an engagement mechanism 35 that can act in conjunction with a drill guide adjustment mechanism 27 (see FIG. 2) to rotate one or more drill guides 31 (see FIG. 2).

A surgeon can use the outer profile 39 of the body 44 to envision a placement of a tibial prosthesis to be implanted, and when the tibial implant template 34 is in a position that the surgeon desires to place the tibial prosthesis, the drill guides 31 can ensure that drilling of guide pin holes is performed accurately. The tibial implant template 34 can have numerous and varied sizes, shapes, and holes relating to sizes, shapes, and connection schemes of tibial prostheses to be implanted. In the present example, a hole 38 is provided in the tibial implant template 34 where a hole would need to be drilled to install a particular tibial prosthesis. A tibial prosthesis can include a keel-like structure on its distal surface. A slot 36, provided in the tibial implant template 34, can be used to visualize the keel position.

It should be noted that any number of positional indicators and aids can be incorporated into the tibial implant template 34. A surgeon can have available to him/her a set of differently sized tibial implant templates 34 to accommodate differently sized bone structures. Tibial implant template sets can also match features of specific tibia implant prosthesis types or models.

Figure 4:
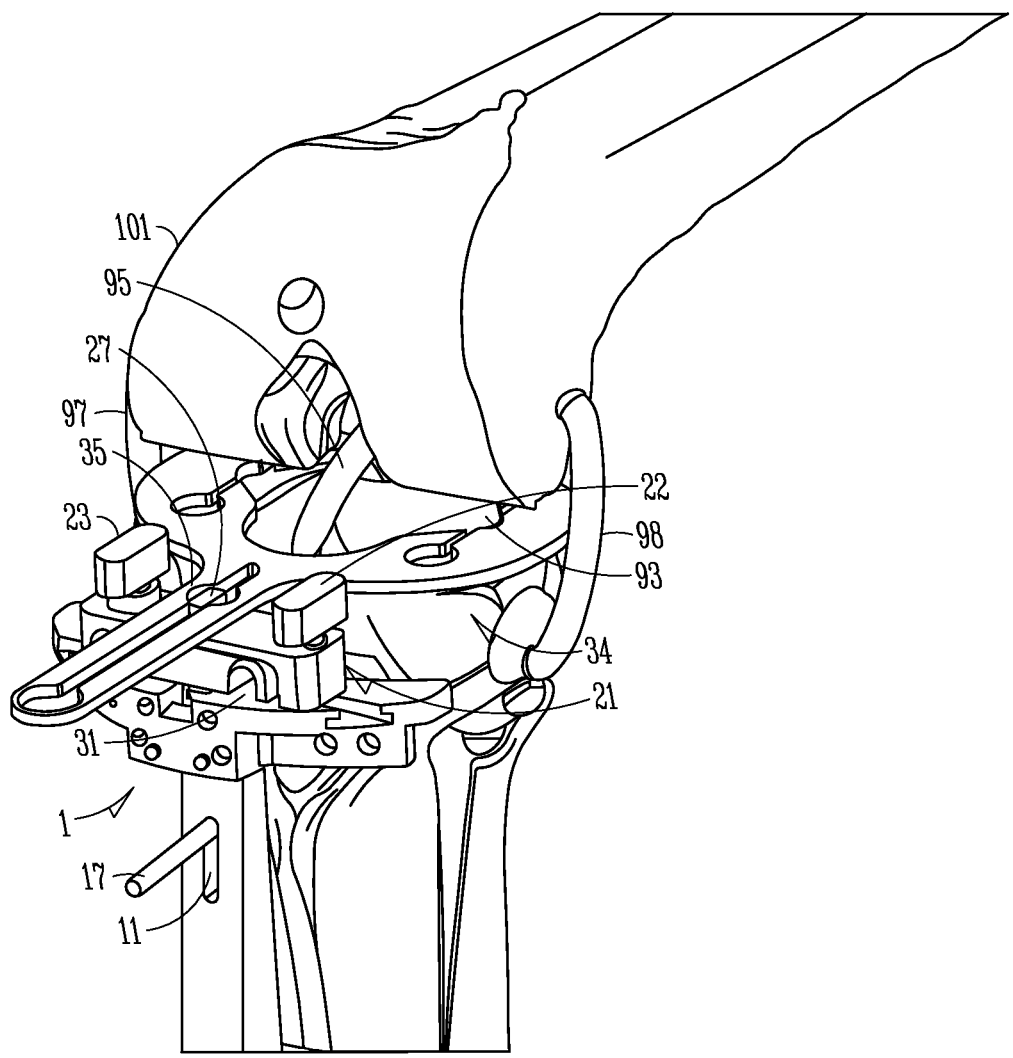
FIG. 4 illustrates a schematic view of a tibial implant template and an adjustment of one or more drill guides included in an alignment guide.

FIG. 4 illustrates an alignment guide 21 positioned on a tibial block 1. A tibial implant template 34 has been inserted between the proximal end of the tibia 93 and the distal end of the femur 101. An outer profile 39 of the tibial implant template 34 is inside both of the MCL 97 and the LCL 98. An interior of the tibial implant template 34 is shaped so that it does not disturb the ACL 95.

As shown, the tibial implant template 34 can be positioned so that an engagement mechanism 35 can rotate a drill guide adjustment mechanism 27 to properly position one or more drill guides 31. The engagement mechanism 35 can be in the form of a slot to allow movement of the tibial implant template 34 in the anterior/posterior direction. Any rotational movement of the tibial implant template 34, however, can cause the engagement mechanism 35 to rotate the drill guide adjustment mechanism 27 and change the position of the one or more drill guides 31. During movement of the drill guides 31, the first tightening screw 22 can be tightened. After proper positioning of the tibial implant template 34, a second tightening screw 23 can be tightened and the drill guides 31 can be secured and ready for drill guiding operation.

Figure 5:
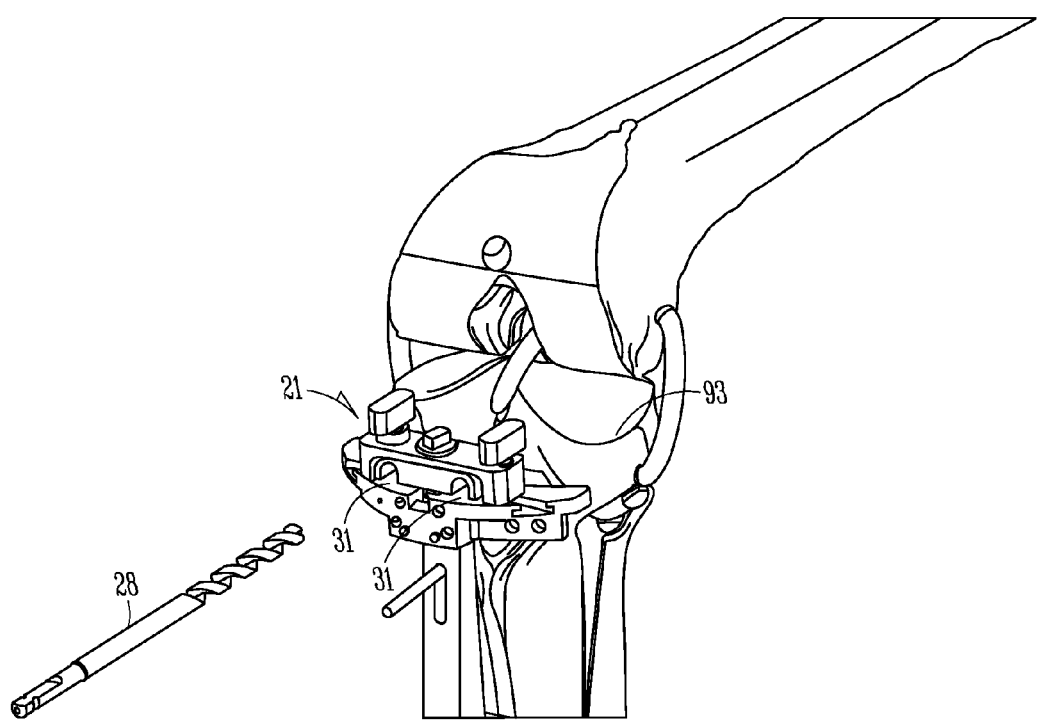
FIG. 5 illustrates a schematic view of a drill advancing into a drill guide included in an alignment guide.

FIG. 5 illustrates a drill (e.g., a drill bit) 28 advancing into a drill guide 31 of an alignment guide 21. The drill 28 can be used to create one or more holes 32 (see FIG. 6) in the proximal end of the tibia 93.

Figure 6:
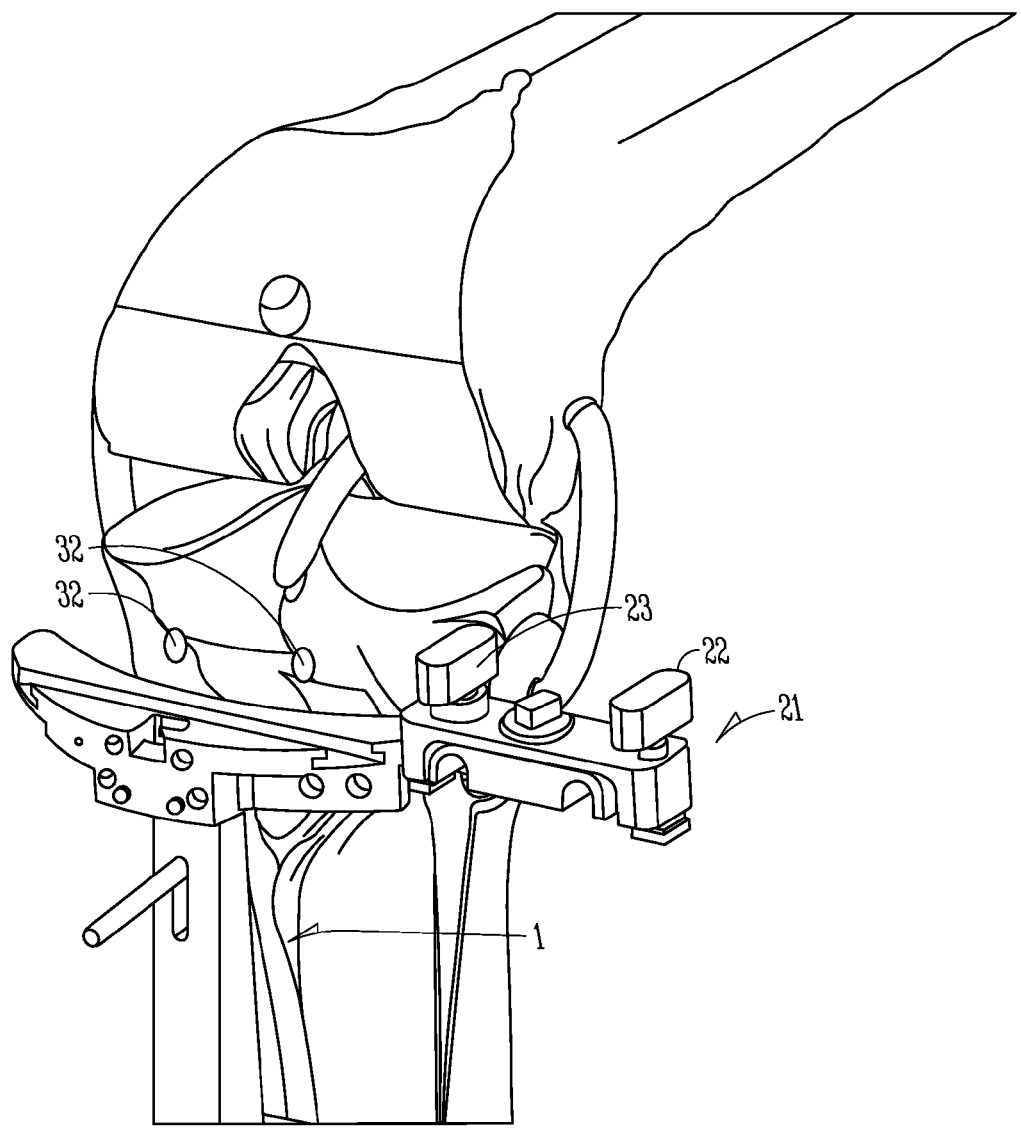
FIG. 6 illustrates a schematic view of a tibia including visible drill holes formed using drill guides, of an alignment guide, as the alignment guide is removed.

FIG. 6 illustrates the removal of an alignment guide 21 from a tibial block 1. After tightening screws 22, 23 have been loosened, the alignment guide 21 can be removed. Drill holes 32 can then visible above the tibial block 1.

Figure 7:
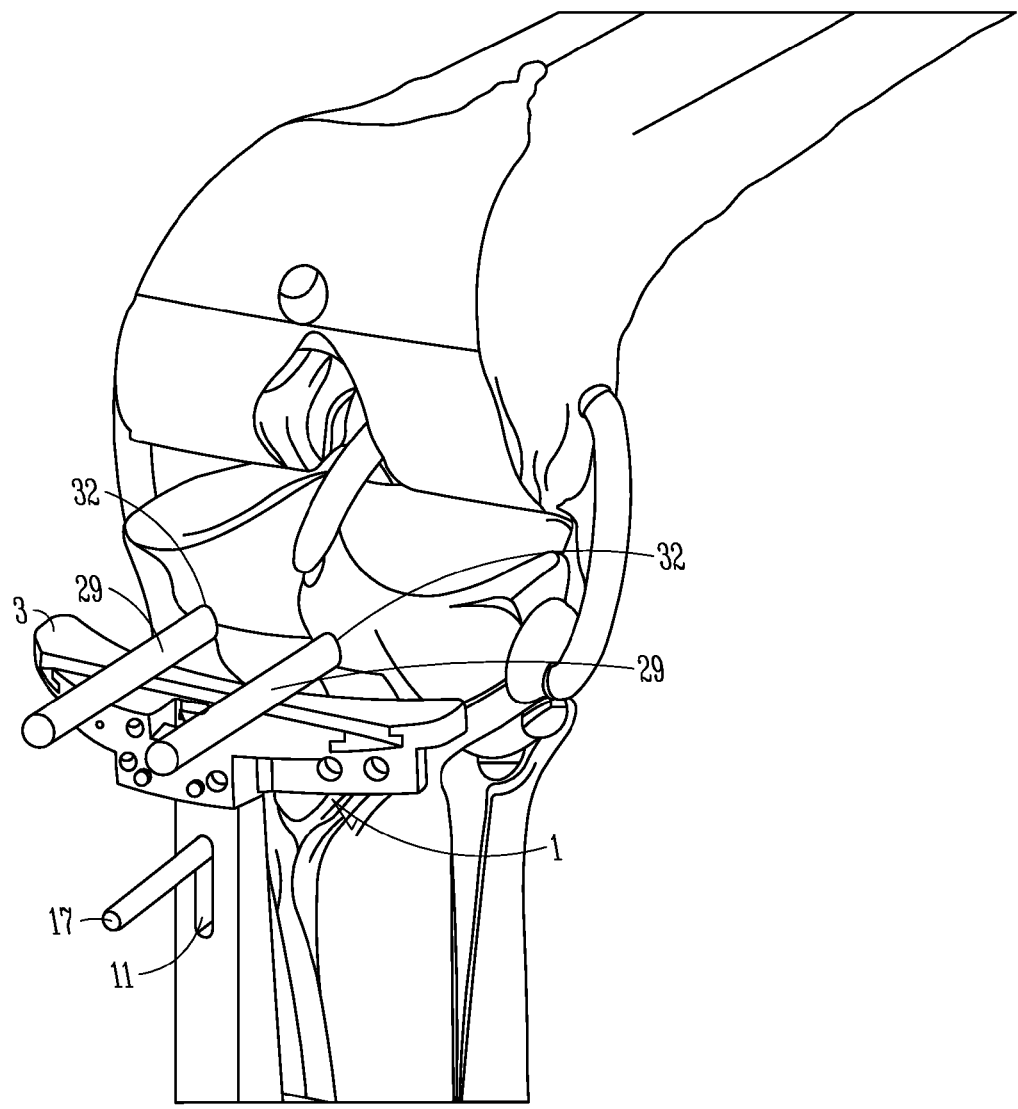
FIG. 7 illustrates a schematic view of guide pins inserted into drill holes, which are formed using drill guides included in an alignment guide.

FIG. 7 illustrates two guide pins 29 installed in two drill holes 32. The guide pins 29 can rest upon a horizontal guide surface 3 of a tibial block 1.

Figure 8:
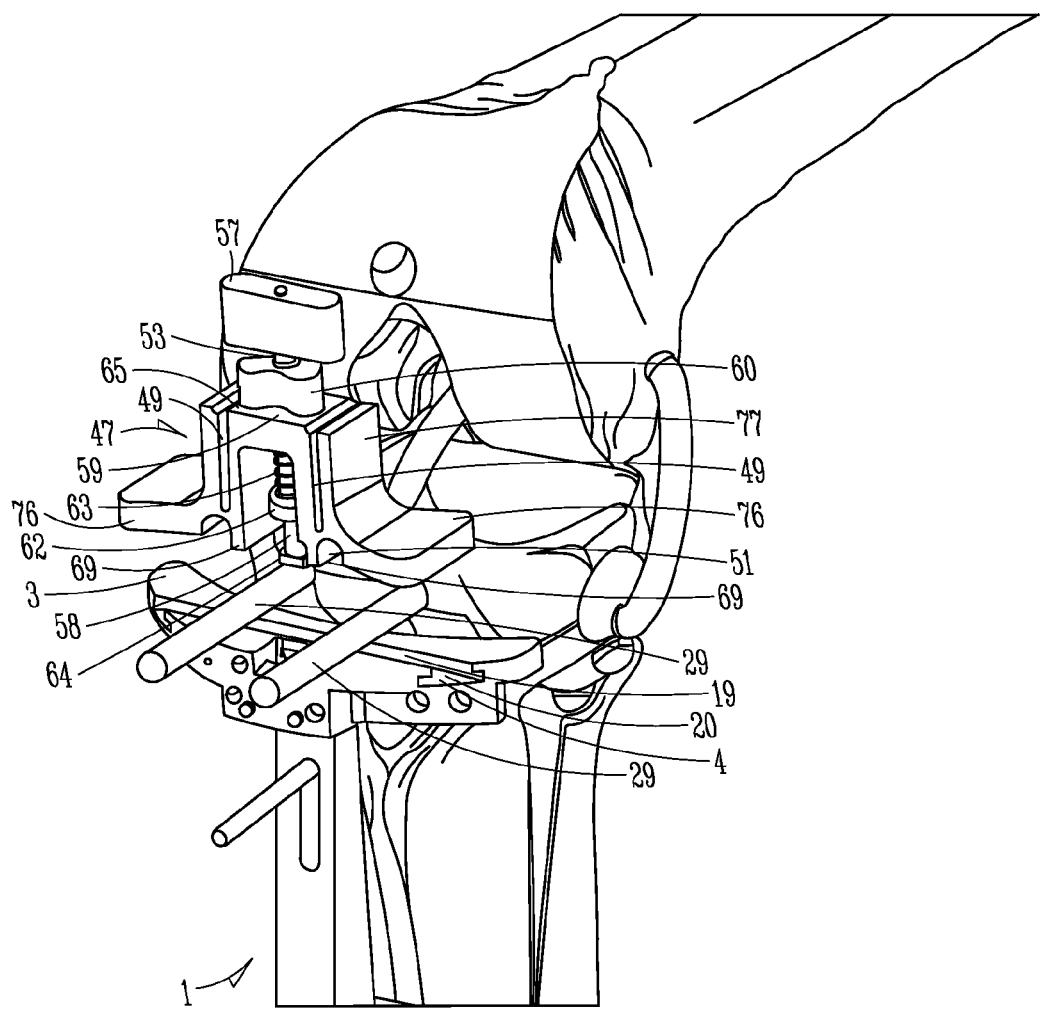
FIG. 8 illustrates a schematic view of a cutting guide being positioned upon guide pins.

FIG. 8 illustrates a cutting guide 47 advancing towards two installed guide pins 29 and a horizontal guide surface 3 of a tibial block 1. The cutting guide 47 can include one or more pin recesses 51 that mate and engage with the installed guide pins 29. The cutting guide 47 can include a main body 77 that can serve as the main structural unit of the cutting guide 47. The pin recesses 51 can be formed in the distal portion of the main body 77. One or more vertical cut slots 49 can guide a vertical saw blade 66 (see FIG. 9). The main body 77 can include mating body members 69 that engage the horizontal guide surface 3 when the cutting guide 47 is in place on the tibial block 1. Lateral extensions 76 can extend outwardly on both sides of the main body 77 and can be configured to not touch the horizontal guide surface 3, thereby forming a horizontal cut slot 48, when the cutting guide 47 is installed, to guide a horizontal saw blade 67 (see FIG. 9).

After the cutting guide 47 has been lowered, the pin recesses 51 can rest against the installed guide pins 29 and the mating body members 69 can rest against the horizontal guide surface 3. The cutting guide 47 can be secured into the alignment guide retaining structure 20 by pushing distally on a bolt handle 57 against pressure provided by a spring 63. Other resilient means could be provided in this location, such as a flat spring or a rubber bushing. After the bolt handle 57 has been depressed, it can be rotated (e.g., 90 degrees) and a bolt plate 64 can engage the alignment guide retaining structure 20. The bolt plate 64 can be disposed at the distal end of a bolt 58, which passes through a bolt hole 59 in the main body 77. The bolt can be threaded (not shown) in a proximal portion. The bolt can also pass through a washer 62 or other structure used as a distal resting surface for the spring 63. The nut 60 can include internal threads (not shown) that mate with the threads of the bolt 58. The bolt plate 64 and the bolt 58 can have a width that is narrow enough to be vertically plunged into the neck region 19 of the slot 4. The bolt plate 64 can have a length longer than the opening of the neck region 19 of the slot 4. The bolt plate 64 can be connected to the bolt 58, which is connected to the bolt handle 57. When the bolt handle is 57 rotated (e.g., rotated 90 degrees), the bolt plate length can engage the surfaces of the alignment guide retaining structure 20. After the bolt plate 64 has been rotated into position, the nut 60 can be rotated until it tightens against a proximal surface 65 of the main body 77. This action can tighten the bolt plate 64 against the alignment guide retaining structure 20 and the cutting guide 47 can be secured and ready for use. The cutting guide 47 can have a detent 53 to provide a position stop for the bolt handle 57 or the cutting guide 47 can have other positioning means, such as a marker, to show that the bolt plate 64 is ready for removal or tightening. The lengthwise direction of the bolt plate 64 can be aligned with the lengthwise direction of the bolt handle 57 as a positioning means.

Figure 17:
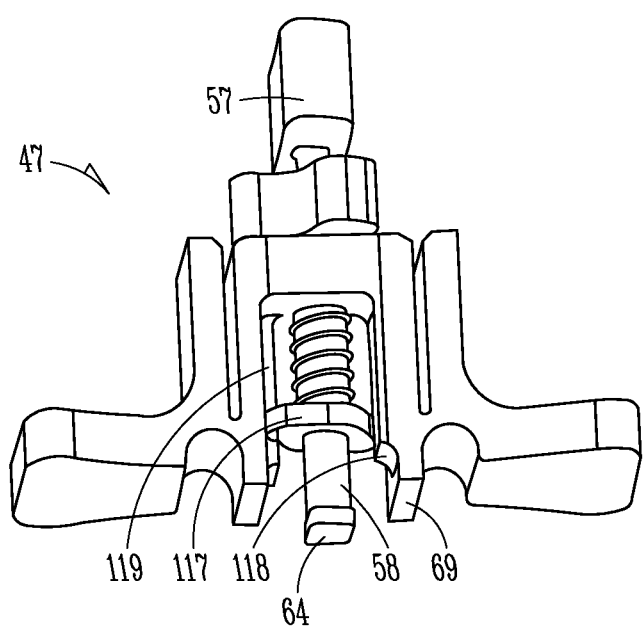
FIG. 17 illustrates an isometric view of a cutting guide.

FIG. 17 illustrates a closer view of the cutting guide 47, as constructed in accordance with at least one example. A lengthwise direction of the bolt plate 64 can be in a position that is transverse to a direction of the slot 4 (see FIG. 8). A locking washer 117 can prevent the bolt handle 57 from further rotation when it contacts a locking bar 119. If the bolt handle 57 is depressed, the locking washer 117 can pass through the washer recess 118 and the lengthwise direction of the bolt plate 64 can be aligned with the lengthwise direction of the slot 4 (see FIG. 8).

Figure 9A:
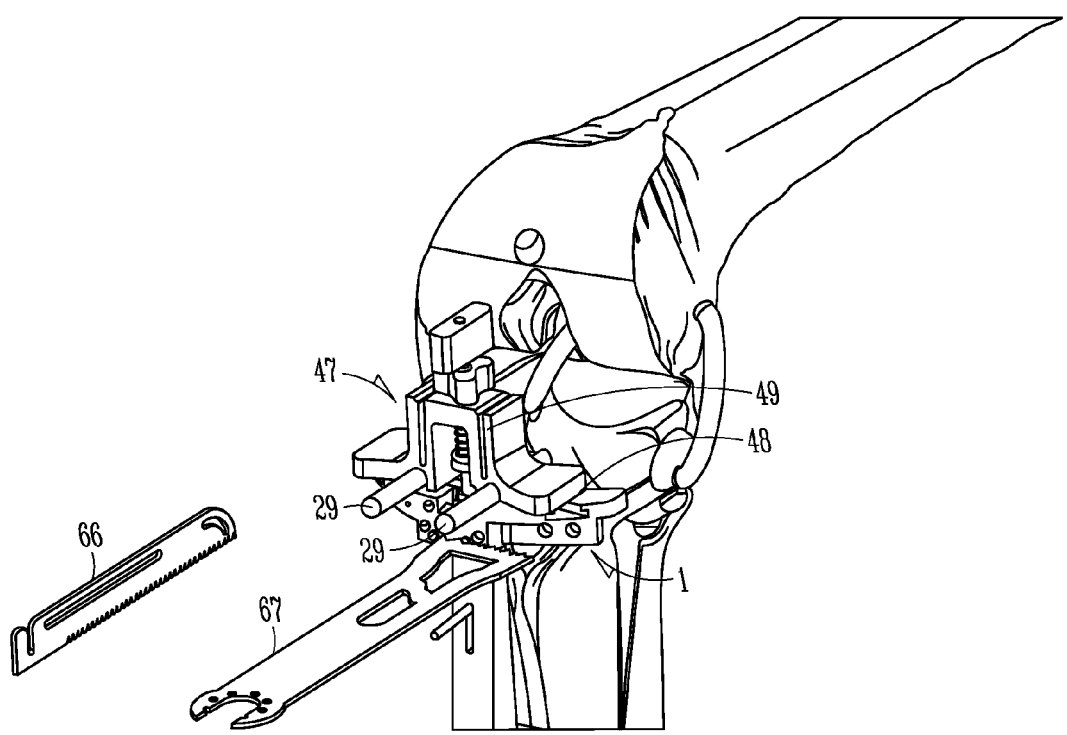
FIG. 9A illustrates a schematic view of a cutting guide, secured on guide pins, and saw blades for the creation of horizontal and vertical cuts.

FIG. 9A illustrates a cutting guide 47 secured in place on top of a tibial block 1. A horizontal saw blade 67 can be used to make a horizontal cut 78 in the proximal end of the tibia 93 and a vertical saw blade 66 can be used to make a vertical cut 73 (see FIG. 9B) in the tibia 93. The cut slots 48, 49 can be positioned so that when a cut is being made, installed guide pins 29 provide a stop for the saw blades 66, 67.

Figure 9B:
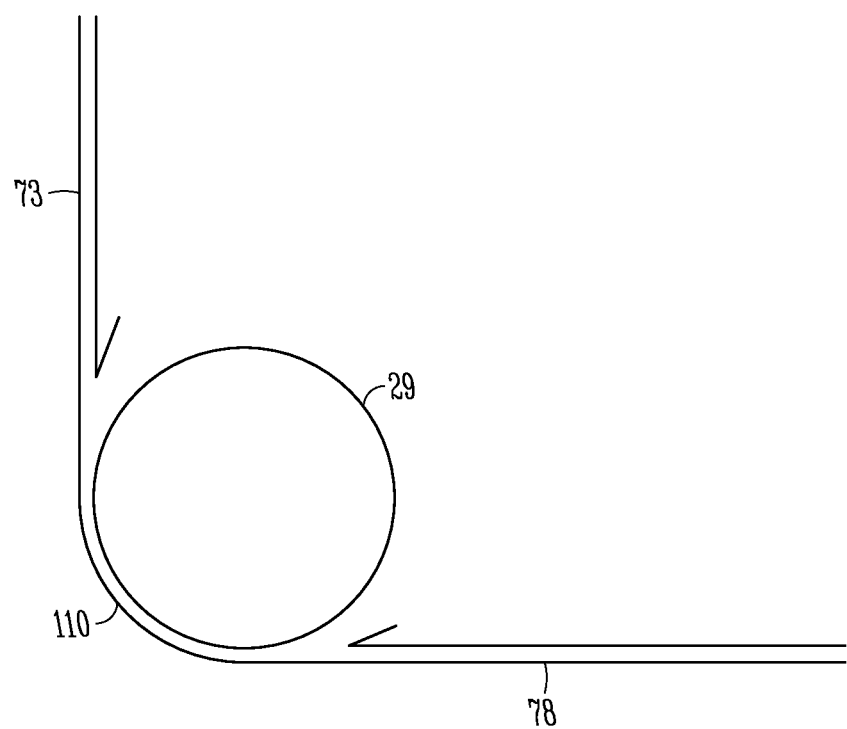
FIG. 9B illustrates a close up plan view of a corner radius of a tibial bone block, formed by horizontal and vertical cuts that are aligned with an outer surface of a guide pin.

The cut slots can be positioned so that the horizontal saw blade 67 intersects a guide pin 29 near its distal outer surface and the vertical saw blade 66 intersects the guide pin on its outer surface positioned adjacent to the center of the tibia 93. FIG. 9B shows a detail of how a vertical cut 73 and a horizontal cut 78 can relate to outer surface portion of a guide pin 29. The finished cut can provide a smooth transition between a drill hole, into which the guide pin 29 is positioned, and the saw blade cuts, thereby giving the finished tibial bone block 104 (see FIG. 12) a smooth radius on an inside corner 110.

Figure 10:
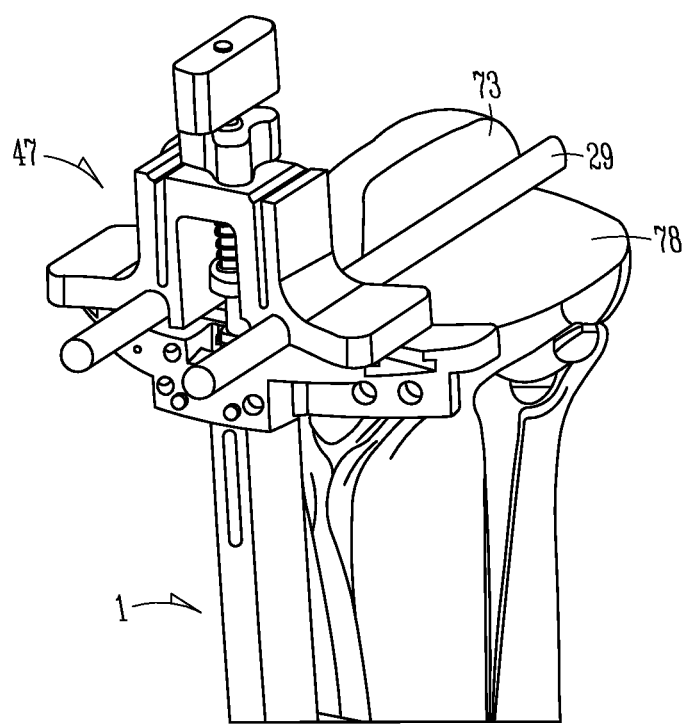
FIG. 10 illustrates a schematic view of a resected tibial bone block, with guide pins in place.

FIG. 10 illustrates a completed horizontal cut 78 and a completed vertical cut 73 with guide pins 29 and a cutting guide 47 remaining in an installed position. Resected bone pieces (not shown) of the tibial 93 have been removed. The cutting guide 47, tibial block 1, and guide pins 29 can now be removed.

Figure 11:
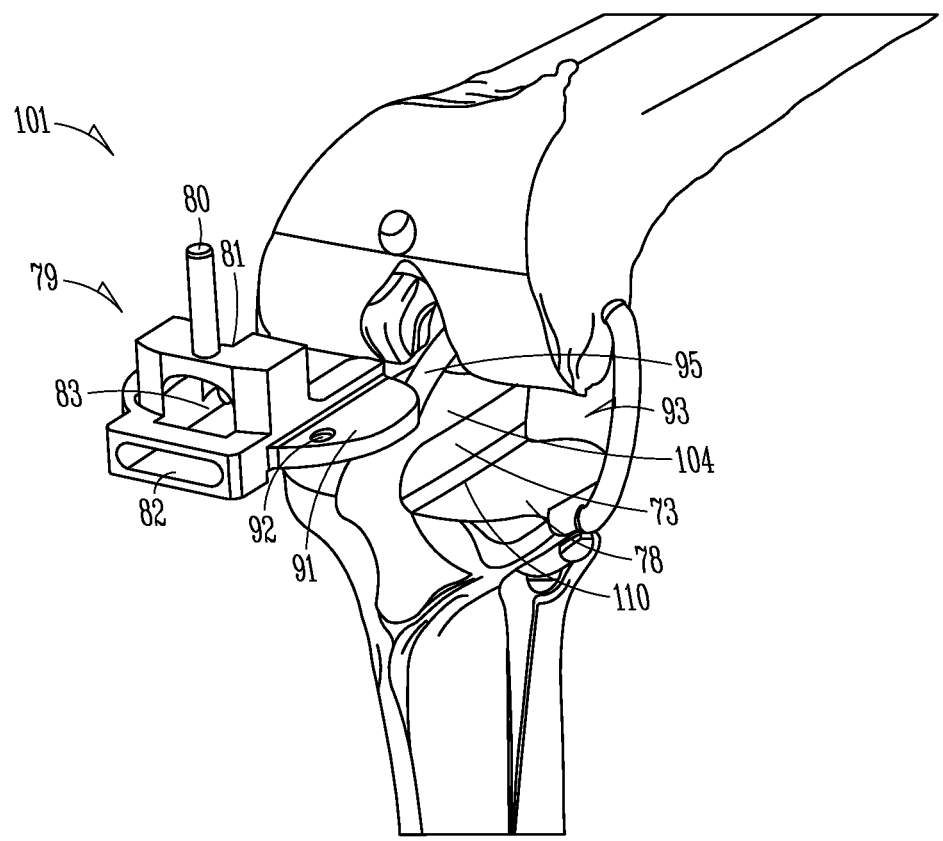
FIG. 11 illustrates a schematic view of a chisel and mill guide being installed on a tibial bone block.

FIG. 11 illustrates an installation of a chisel and mill guide 79 onto a resected tibia 93. The chisel and mill guide 79 can be used to finish a formation of a tibial bone block 104 by forming an area anterior to the ACL 95, where a portion of a tibial prosthesis connecting medial and lateral prosthesis portions can be disposed without disturbance to a bone connection of the ACL 95.

Figure 12:
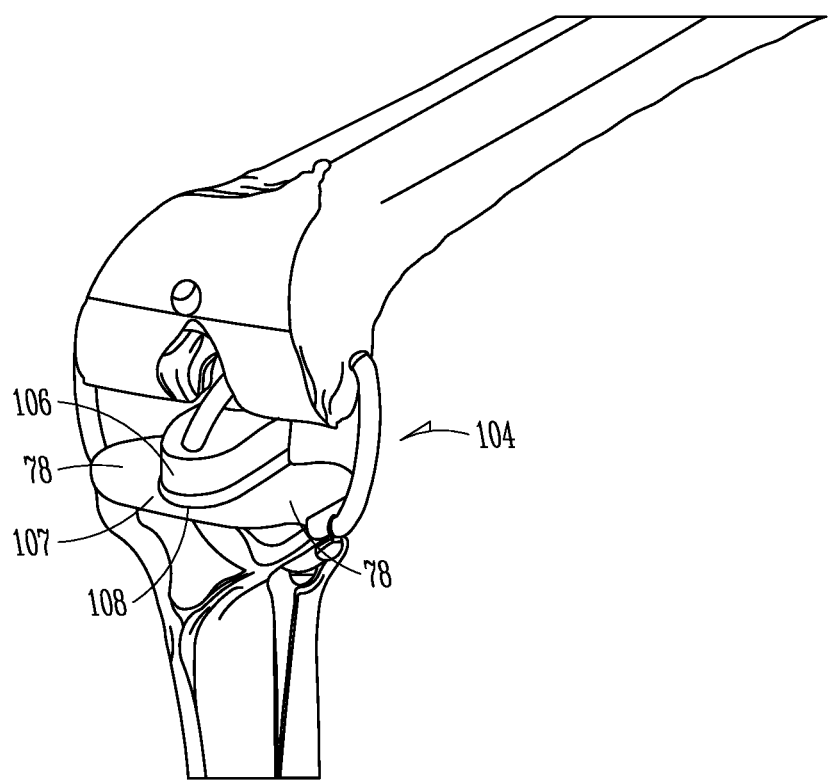
FIG. 12 illustrates a schematic view of a finished tibial bone block and retained cruciate ligaments.

FIG. 12 represents an example of a finished tibial bone block 104. The chisel and mill guide 79, in conjunction with a chisel and a mill, can form an anterior horizontal surface 107 that matches a proximal height of horizontal cuts 78, and a curved vertical surface 106 that is the most anterior vertical surface of the finished tibial bone block 104. The chisel and mill guide 79 can also aid in forming a curved inside radiused corner 108, which joins the curved vertical surface 106 and the anterior horizontal surface 107.

Returning to FIGS. 11 and 13, the chisel and mill guide 79 can include a set of guide arms 91 configured to fit between the tibia 93 and the femur 101 and around the resected cuts in the tibia. A pin protrusion 80 and a chisel recess 81 can form a rigid placement mechanism for a chisel 109 (shown in FIG. 14). A set of nail holes 92 can be included in the guide arms 91 for the securement of the chisel and mill guide 79 to the tibia 93. A mill guide 82 can be configured to aid in milling an anterior horizontal surface 107 (see FIG. 12) and a curved inside radiused corner 108 (see FIG. 12). The chisel and mill guide 79 can include radiused mating edges 83 on the guide arms 91, which fit closely to a vertical cut 73 and an internal corner 110, while a lower surface of the arms 91 rests on the completed horizontal cut 78.

Figure 13:
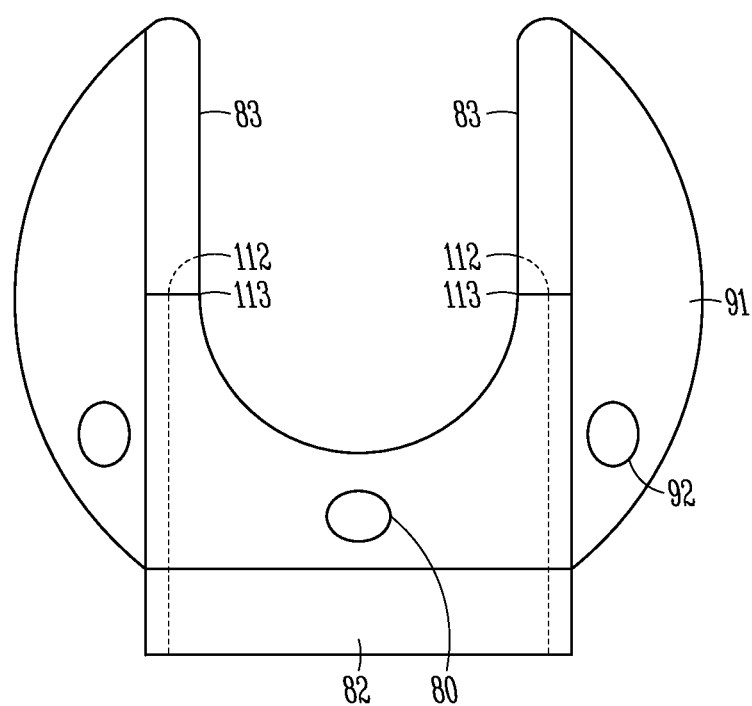
FIG. 13 illustrates a top view of a chisel and mill guide.

As shown in FIG. 13, the mill guide 82 can be configured with a furthest reach 112, which can be slightly past a junction 113 of the curved recess 81 and the straight internal portion of the guide arms 91. The radiused mating edge 83 does not extend to the junction 113 so that a tip of a ball end mill can be inserted in a posterior direction far enough to form a smooth transition between the inside corner radius 110 and the curved inside corner radius 108.

Figure 14:
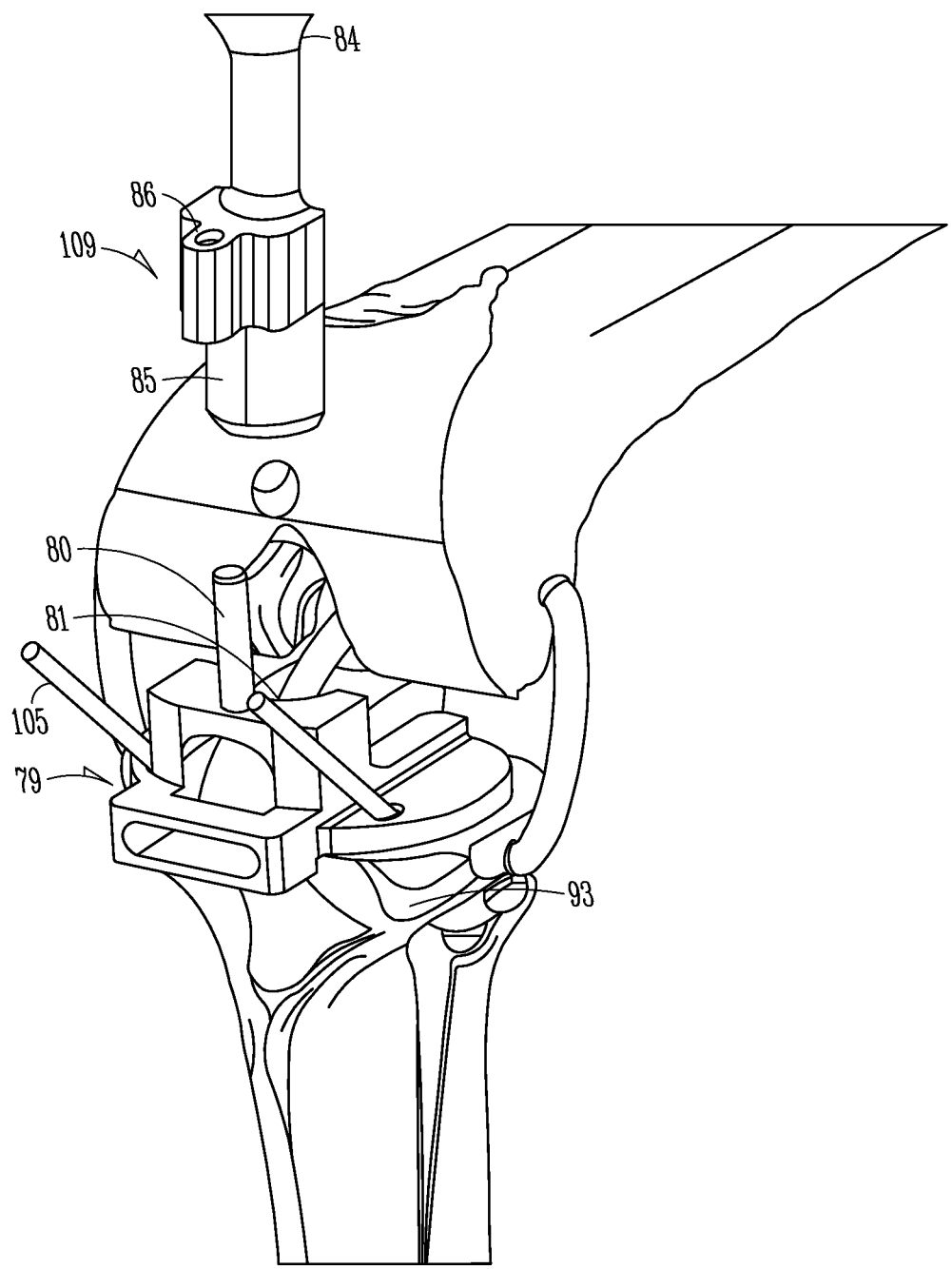
FIG. 14 illustrates a schematic view of a chisel and mill guide pinned in place and an advancing chisel.

FIG. 14 illustrates a chisel and mill guide 79 placed on a resected proximal tibia 93 and as far posterior as a surgeon determines a chisel cut should be made. The chisel and mill guide 79 can be secured to the tibia 93 by screws, pins, nails, or other means and is shown secured by nails 105. A chisel 109 can include a blade 85 and a handle 84. It should be noted that in this example a chisel recess 81 is shown as curved, but it can take other shapes. The back of the blade 85 can mate with the chisel recess 81 as a mating void 86 is engaged with a pin protrusion 80. The chisel 109 can be secured in each direction except for slidable movement upon the pin protrusion 80.

Figure 15:
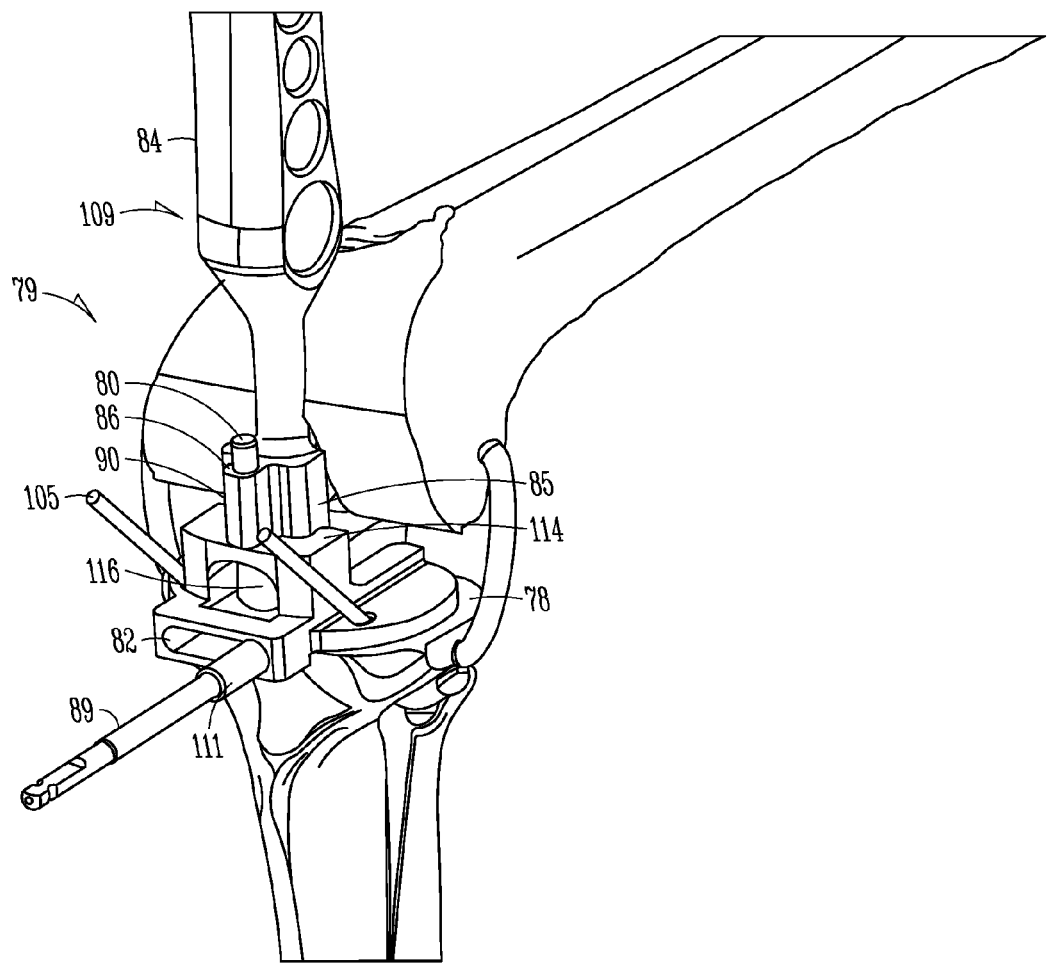
FIG. 15 illustrates a schematic view of a chisel and a ball end mill, each of which is engaged with a chisel and mill guide.

FIG. 15 illustrates a chisel 109 after it has been advanced into its final position and has cut a curved vertical surface 106 (see FIG. 12) of the tibia 93. The chisel handle 84 can be configured to withstand impact blows. Pins 105 can be used to retain the chisel and mill guide 79 and the pin protrusion 80 can aid in locating and retaining the chisel 109. A mating void 86 can have a depth limitation structure 90 that prevents the chisel 109 from further cutting movement when the depth limitation structure 90 abuts a body proximal face 114 of the chisel and mill guide 79. The depth limitation structure 90 can also be disposed at other locations on the chisel 109. With the chisel 109 at the limited depth, a mill 89 can be inserted into a mill guide 82 and bone material can be removed that is anterior of the chisel 109 and proximal to the height of the horizontal cuts 78. The mill guide 82 can be formed so that the milled cut will match the horizontal cuts 78. The mill 89 can have a rounded cutting end so that it will form an inside radiused corner. A back 116 of the chisel 109 can be used as a mill stop. At the medial and lateral edges of a chisel blade 85, the mill 89 would no longer be stopped, but can have a mill limit 111 on the mill 89 to prevent the mill from entering the tibial bone block 104, by abutting the mill guide 82. As recited above, a cutting guide 47 can allow a final reach 112 (see FIG. 13) so that the mill 89 can enter the mill guide 82 far enough to provide a smooth transition between the inside corner radius 110 and the curved inside corner radius 108 (see FIG. 11).

Figure 16:
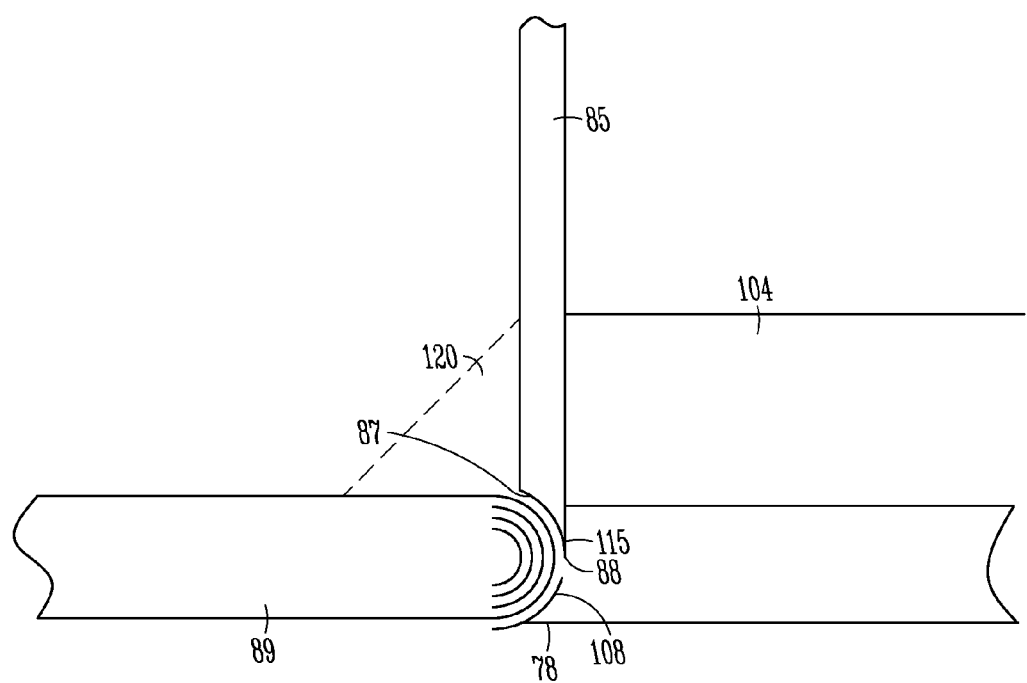
FIG. 16 illustrates a plan view of a fluted chisel blade tip acting as a travel stop for a ball end mill.

FIG. 16 illustrates a close up plan view of a mill 89 with an anterior face of a chisel tip 88 of the chisel blade 85 acting as a cutting stop 115 to prevent the mill 89 from entering a tibial bone block 104. The chisel tip 88 can have a fluted anterior face 87 that aids the mill 89 in locating to a correct depth for cutting the radiused curved inside corner 108. The horizontal cut is shown at 78. Bone that is being removed is depicted by the dashed line and element numeral 120.

The above Detailed Description includes references to the accompanying drawings, which form a part of the Detailed Description. The drawings show, by way of illustration, specific embodiments in which the present tibial resection systems and methods can be practiced. These embodiments are also referred to herein as "examples." Such examples can include elements in addition to those shown or described. However, the present inventors also contemplate examples in which only those elements shown or described are provided.

The above Detailed Description is intended to be illustrative, and not restrictive. For example, the above-described examples shown or described (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

In the appended claims, the terms "including" and "in which" are used as the plain-English equivalents of the respective terms "comprising" and "wherein." The terms "including" and "comprising" are open-ended, that is, a system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A tibial resection system, comprising:
    a tibial block, couplable to an anterior side of a tibia, longitudinally extending from a proximal end portion to a distal end portion;
    an alignment guide, couplable to the proximal end portion of the tibial block, including one or more drill guides and a drill guide adjustment mechanism; and
    a tibial implant template, engageable with the drill guide adjustment mechanism such that rotational movement of the tibial implant template adjusts an axial direction of the one or more drill guides;
    wherein the proximal end portion of the tibial block includes a guide surface having a slot, the slot extending in a direction perpendicular to the longitudinal extension of the tibial block and configured to receive a coupling projection of the alignment guide, the slot includes a T-shaped cross-section, and the coupling projection includes a size and shape engageable with the T-shaped cross-section.

2. The system of claim 1, wherein an outer profile of the tibial implant template substantially matches an outer profile of a tibial prosthesis to be implanted.

3. The system of claim 1, wherein the tibial implant template is sized and shaped to fit in situ between a proximal end of the tibia and a distal end of a femur, between medial and lateral collateral ligaments, and partially around one or more cruciate ligaments.

4. The system of claim 1, further comprising one or more guide pins insertable into one or more drill holes formed using the one or more drill guides.

5. The system of claim 4, further comprising a cutting guide, positionable on the one or more guide pins, including one or more vertical cut slots and one or more horizontal cut slots.

6. The system of claim 5, wherein the one or more horizontal cut slots and the one or more vertical cut slots are positioned to substantially align with an outer surface of the one or more guide pins, when the cutting guide is positioned thereon.

7. The system of claim 1, further comprising a chisel and mill guide having a proximal end portion, including a pin projection and a curved recess wall; a distal end portion, positionable on a resected tibial surface; and an anterior portion, including a mill recess.

8. The system of claim 7, wherein the pin projection is configured to receive a mating void of a chisel handle and the curved recess wall is configured to receive and guide a chisel blade.

9. The system of claim 7, wherein an extension of the curved recess wall intersects with a depth of the mill recess.

10. A tibial resection system, comprising:
    a tibial block, couplable to an anterior side of a tibia, longitudinally extending from a proximal end portion to a distal end portion;
    an alignment guide, couplable to the proximal end portion of the tibial block, including one or more drill guides and a drill guide adjustment mechanism; and
    a tibial implant template, engageable with the drill guide adjustment mechanism such that rotational movement of the tibial implant template adjusts an axial direction of the one or more drill guides, wherein the tibial implant template includes one or more holes positioned to match a location of one or more holes of a tibial prosthesis to be implanted.

11. A tibial resection system, comprising:
    a tibial block, couplable to an anterior side of a tibia, longitudinally extending from a proximal end portion to a distal end portion;
    an alignment guide, couplable to the proximal end portion of the tibial block, including one or more drill guides and a drill guide adjustment mechanism, wherein the alignment guide comprises a first member, including the one or more drill guides, and a second member positioned proximally of the first member, the first and second members pivotably connected and moveable, relative to one another, using the drill guide adjustment mechanism; and
    a tibial implant template, engageable with the drill guide adjustment mechanism such that rotational movement of the tibial implant template adjusts an axial direction of the one or more drill guides.

* * * * *